United States Patent [19]

Kornettka et al.

[11] Patent Number: 5,324,505
[45] Date of Patent: Jun. 28, 1994

[54] STRIPED, MULTICOLORED TOOTHPASTE AND DISPENSER THEREFOR

[75] Inventors: Norbert Kornettka, Duesseldorf; Franz Foerg, Langenfelod; Albert Stoeffler, Duesseldorf; Juergen Fiedler, Nettetal, all of Fed. Rep. of Germany

[73] Assignee: Henkel Kommanditgesellschaft auf Aktien, Duesseldorf, Fed. Rep. of Germany

[21] Appl. No.: 689,063

[22] PCT Filed: Dec. 4, 1989

[86] PCT No.: PCT/EP89/01476

§ 371 Date: Aug. 9, 1991

§ 102(e) Date: Aug. 9, 1991

[87] PCT Pub. No.: WO90/06744

PCT Pub. Date: Jun. 28, 1990

[30] Foreign Application Priority Data

Dec. 12, 1988 [DE] Fed. Rep. of Germany ....... 3841775

[51] Int. Cl.⁵ .......................... A61K 7/16; B67C 3/02; B05B 7/00; B65D 35/24
[52] U.S. Cl. ....................................... 424/49; 141/100; 222/94
[58] Field of Search .............................. 424/7.1, 49-58

[56] References Cited

U.S. PATENT DOCUMENTS

| 3,178,770 | 4/1965 | Willis | 18/12 |
|---|---|---|---|
| 3,240,393 | 3/1966 | Jablonski | 222/94 |
| 3,488,419 | 1/1970 | McCune et al. | 424/49 |
| 3,881,529 | 5/1975 | Mannara | 141/100 |
| 3,924,784 | 12/1975 | Smrt | 222/176 |
| 3,941,772 | 3/1976 | Ploger et al. | 260/239 B |
| 3,952,782 | 4/1976 | Mannara | 141/100 |
| 4,389,181 | 6/1983 | Frick | 425/461 |
| 4,691,847 | 9/1987 | Ford et al. | 222/259 |
| 4,715,518 | 12/1987 | Moore, III | 222/157 |

FOREIGN PATENT DOCUMENTS

| 0047393 | 3/1982 | European Pat. Off. |
|---|---|---|
| 0076563 | 4/1983 | European Pat. Off. |
| 0178377 | 4/1986 | European Pat. Off. |
| 251661 | 1/1988 | European Pat. Off. |
| 318835 | 11/1988 | European Pat. Off. |
| 1185981 | 9/1965 | Fed. Rep. of Germany |
| 2224430 | 5/1972 | Fed. Rep. of Germany |
| 2343196 | 3/1975 | Fed. Rep. of Germany |
| 2454136 | 6/1975 | Fed. Rep. of Germany |
| 2512849 | 10/1976 | Fed. Rep. of Germany |
| 3507134 | 1/1986 | Fed. Rep. of Germany |
| 3904599 | 8/1990 | Fed. Rep. of Germany |
| 92/12063 | 7/1992 | PCT Int'l Appl. |
| 813514 | 5/1959 | United Kingdom |
| 1271944 | 4/1972 | United Kingdom |
| 1394172 | 5/1975 | United Kingdom |
| 1418695 | 12/1975 | United Kingdom |
| 2109230 | 6/1983 | United Kingdom |
| 2161863 | 1/1986 | United Kingdom |

OTHER PUBLICATIONS

U.S.P.T.O. Translation of German DE 1185981 Sep. 16 1965 (Evans) (6 pages).
Bernard Idson, Ph. D., "Rheology: Fundamental Concepts", *Cosmetics and Toiletries*, vol. 93, Jul. 1978, pp. 23-30.

*Primary Examiner*—Shep K. Rose
*Attorney, Agent, or Firm*—Wayne C. Jaeschke; Norvell E. Wisdom, Jr.; Henry E. Millson, Jr.

[57] ABSTRACT

Strands of multicolored, striped toothpaste, more especially with a cross-section in the form an n-sided polygon, where n is an integer of 3 to 7, can be dispensed without diffuse transition zones from a storage container providing the ratio between the yield points of the carrier strand paste and the stripe paste is approximately 1.10:1 to 1.20:1. A device of the type shown in FIG. 1 is suitable for dispensing the toothpaste.

14 Claims, 1 Drawing Sheet

STRIPED, MULTICOLORED TOOTHPASTE AND DISPENSER THEREFOR

BACKGROUND OF THE INVENTION

1. Field of the Invention

This invention relates to toothpastes in the form of a multicolored, striped strand and to a device for dispensing the strand from a container.

2. Statement of Related Art

In the field of personal hygiene and cosmetic products, ever increasing importance is being attributed not only to the corresponding ingredients, but also to an attractive presentation. Apart from pure aesthetics, which play an important part in regard to the choice of color, pack and, in many cases, the consistency of the product, there are also practical aspects to be taken into account in this regard. For example, the pleasure which children find in colors and shapes can be directed towards encouraging them to familiarize themselves, so to speak at play, with the necessities involved in cleanliness and personal hygiene. One way of encouraging children to brush their teeth regularly is to provide them with a colored, preferably multicolored, toothpaste distinguished by an attractive shape of the strand and optionally provided with an agreeable flavor.

Toothpastes with incorporated centers or stripes are known. Thus, DE-OS 19 37 001 describes toothpastes in which stripes or centers of a paste-like mass of high cleaning power are incorporated in a gel-like carrier strand. The opposite case, where transparent stripes are incorporated in a carrier strand of opaque toothpaste of high cleaning power, is described in European patent application 76 563. In both specifications, it is pointed out that the constituent pastes of the carrier strand and the stripe should have the same rheological properties. Further examples of striped toothpastes can be found in DE-OSS 16 17 907 and 24 54 136.

Striped toothpaste strands are normally produced by the two pastes of the carrier strand and the stripe being dispensed simultaneously when pressure is applied to the storage container. The desired appearance of the toothpaste strand is determined by corresponding design of the outlet opening of the storage container. Information on the filling of corresponding toothpaste tubes and on the configuration of the outlet opening of those tubes can be found, for example, in DE-PS 11 85 981 or GB-PS 813, 514.

Known striped toothpastes have a substantially circular and generally unstable strand cross-section. In addition, a diffuse transition is often formed between the carrier strand and the stripe.

This transition zone should be eliminated to enhance the aesthetic appearance of the strand. In addition, there is a need for toothpaste strands of polygonal cross-section which have an improved hold on toothbrushes. This is of particular interest when the toothbrushes are used by children. The stripes of different color may be situated at the corners of such a strand of toothpaste.

To this end, the constituent pastes of the carrier strand and the stripe should be coordinated with one another in such a way that they can be dispensed synchronously and uniformly from a container, the stripe paste being intended in particular to form the corner edges of a polygonal toothpaste strand.

In addition, there is a need for a device which enables the two coordinated phases of the toothpaste to be synchronously and uniformly dispensed.

DESCRIPTION OF THE INVENTION

Objects of the Invention

It has now surprisingly been found that the problem can be solved by formulating the constituent pastes of the carrier strand and the stripe in such a way that they differ specifically from one another in certain rheological parameters.

Accordingly, the present invention relates to a toothpaste to be dispensed from a container in the form of a multicolored, striped strand, consisting of a carrier strand paste and at least one stripe paste differing in color from the carrier strand paste, characterized in that the ratio between the yield points of the carrier strand paste and the stripe paste is approximately 1.10:1 to 1.20:1.

Toothpastes normally show the rheological behavior of non-newtonian liquids. When a shear stress below a value known as the yield point is applied, the substance behaves like a solid. The substance only flows under shear stresses which are greater than the yield point. The functional correlation between the shear stress applied and the shear rate observed above the yield point can be described by semi-empirical equations of state, such as for example the Bingham equation or the Casson equation. In most cases, the rheological behavior of toothpastes is described quite well by the Casson equation $$D=(\sqrt{\tau}-\sqrt{f_c})^2/\eta$$

in which
D is the shear rate
$\tau$ is the shear stress,
$f_c$ is the yield point (according to Casson) and
$\eta$ is the dynamic viscosity.

Further information on these rheological relations can be found in the relevant specialist literature, cf. for example the Articles by R. R. Zangger in CZ-Chemie-Technik, Vol 3, pp. 283–286 (1974), G. Simon in Chemiker-Zeitung, Vol. 100, pp. 25–34 (1976) and B. Idson in Cosmetics and Toiletries, Vol. 93, pp. 23–30 (1978).

The rheological properties of toothpastes can be determined with commercially available viscosimeters, for example with Haake rotational viscosimeters. In a graph in which the particular shear rate is plotted as a function of the shear stress, the yield point can be read off as known to the expert, optionally by extrapolation of the measuring curve to D=0. If the toothpaste shows a correlation in the form of a hysteresis curve when the shear rate is changed in cycles between 0 and a certain value, the yield point and the viscosity values cited in this application are all based on the so-called upward shear cycle. This is the measurement phase in which the shear rate is increased from 0 to final value. The method used for measurement and evaluation is described in detail in the Examples.

SUMMARY OF THE INVENTION

Toothpastes in which the ratio between the yield points of the carrier strand paste and the stripe paste is 1.12:1 to 1.18:1 and more particularly of the order of 1.15:1 have proved to be particularly suitable for use in accordance with the invention. The absolute values of the yield points of the toothpastes according to the invention at room temperature are in the range from about 65 to 280 Pa.

In addition, it is of advantage if the other rheological properties of the carrier strand paste and the stripe paste differ only slightly from one another. Above all, it is favorable if the dynamic viscosities as measured under stresses above the yield points differ only minimally from one another. For the toothpastes according to the invention, these dynamic viscosities are in a range of from about 0.01 to 0.05 Pa.s at room temperature.

This may be achieved, for example, by ensuring that the carrier strand paste and stripe paste differ only in their content of water and/or other additives used to establish the yield points as well as in their content of dyes and/or pigments. Thus, a single basic mixture may be used to formulate both the carrier strand paste and the stripe paste. The components are then added to this basic mixture.

The toothpastes according to the invention may be produced from the known components in the form of gel-like or paste-like preparations. Typical components are abrasives and polishes, water, humectants, thickeners, surfactants, flavorings, sweeteners, antiseptics and oral toiletries and also dyes.

Suitable abrasives and polishes are, for example, special silicas such as precipitated silicas and gel silicas, aluminum oxide trihydrate, finely divided $\alpha$-aluminum oxide, calcium carbonate, calcium phosphate, magnesium phosphate, water-insoluble sodium metaphosphate, magnesium carbonate and magnesium hydroxide and also mixtures of these compounds. The abrasives and polishes are typically used in quantities of from about 15 to 45% by weight, based on the total weight of the toothpaste.

Suitable humectants are such substances as, for example, polyalcohols such as, for example, glycerol, sorbitol and xylitol.

Suitable thickeners for the preparations are, for example, aerogel silicas, bentonites and hydrocolloids, such as carboxymethyl cellulose, hydroxyethyl cellulose, hydroxypropyl guar, hydroxyethyl starch, polyvinyl pyrrolidone, polyethylene glycols, vegetable gums, such as traqacanth, agar agar, carrageenans, gum arabic and xanthans, and also carboxyvinyl polymers, such as the known Carbopol(R) types.

The toothpastes may also contain surfactants, preferably anionic high-foaming surfactants, such as for example linear sodium alkyl sulfates containing 12 to 18 carbon atoms in the alkyl group, sodium salts of alkyl polyglycol ether sulfates containing 12 to 16 carbon atoms in the linear alkyl group and 2 to 6 glycol ether groups in the molecule, sodium salts of linear alkane ($C_{12-18}$) sulfonates, sulfosuccinic acid monoalkyl ($C_{12-18}$) esters, sulfatized fatty acid monoglycerides, sulfatized fatty acid alkanolamides, sulfoacetic acid alkyl ($C_{12-18}$) esters, acyl sarcosides, acyl taurides and acyl isethionates containing 8 to 18 carbon atoms in the acyl group. Other suitable surfactants are nonionic surfactants, for example ethoxylates of fatty acid monoglycerides and diglycerides, fatty acid sorbitan esters and ethylene oxide/propylene oxide block polymers.

Suitable flavorings are, for example, peppermint oil, curled mint oil, eucalyptus oil, aniseed oil, fennel oil, caraway oil, menthyl acetate, cinnamaldehyde, anethol, vanillin and thymol and also mixtures of these and other natural and synthetic flavorings. It can be of advantage to use flavorings which provide the toothpaste with a fruit flavor, such as a strawberry, raspberry, pineapple, apple or orange flavor.

The toothpastes may contain such substances as saccharin, sodium cyclamate, aspartyl phenylalanine methylester and Acesulfam(R)K and also sucrose, lactose, maltose and fructose as sweeteners.

Antiseptics and oral cosmetics are understood to be preservatives and antimicrobial agents, anti-tartar agents, caries inhibitors, plaque inhibitors and also anti-inflammatory agents.

Suitable preservatives and antimicrobial agents include inter alia p-hydroxybenzoic acid methyl, ethyl and propyl ester, sodium sorbate, sodium benzoate, bromchlorophene, phenyl salicylic acid ester and thymol.

Suitable anti-tartar agents are azacycloheptane-2,2-diphosphonic acid, 1-hydroxyethane-1,1-diphosphonio acid, 1-phosphonopropane-1,2,3-tricarboxylic acid and sodium salts thereof and also the compounds known from U.S. Pat. No. 3,488,419, DE-OS 22 24 430 and DE-OS 23 43 196.

Caries inhibitors are, for example, sodium fluoride, sodium monofluorophosphate and tin fluoride.

Suitable keratogenic and/or anti-inflammatory agents are, for example, allantoin, urea, azulene, camomile active components and acetyl salicylic acid derivatives.

Finally, the toothpastes according to the invention may contain dyes and/or pigments, such as for example titanium dioxide, and also buffers, such as for example primary, secondary or tertiary alkali phosphates or citric acid/sodium citrate.

The additives preferably used to establish the yield points are polyalcohols, more especially sorbitol and/or glycerol, and/or silica.

Toothpastes according to the invention have a particularly advantageous aesthetic appearance when they contain the carrier strand paste and the stripe paste in a ratio by volume of from about 92:8 to about 97:3 and, more particularly, of the order of 95:5.

According to the invention, both the carrier strand paste and also the stripe paste may be formulated independently of one another in such a way that they appear transparent or non-transparent. The corresponding measures, for example the addition of pigments for non-transparent formulations, are known to the expert.

In one preferred embodiment, the toothpaste is dispensed from the storage container as a strand having a cross-section in the form of an n-sided polygon, where n is an integer of 3 to 7, the stripe paste being situated at the corners of the n-sided polygon. In a particularly preferred embodiment, the toothpaste is dispensed as a strand having a cross-section in the form of a rectangle, more especially a square.

The problem addressed by the invention in regard to the device for dispensing the toothpaste is solved by the fact that the outlet opening of the neck has a polygonal, more especially square, cross-sectional area and by the fact that perforations are arranged at the corners of the cross-sectional area.

The invention thus provides an application nozzle for toothpaste containers with which a polygonal strand of toothpaste, in which the stripes form the edges, can be dispensed from the container.

BRIEF DESCRIPTION OF THE DRAWINGS

The device to be used for dispensing the toothpaste according to the invention is described by way of example in the following with reference to the accompanying drawings, wherein:

The device consists of an application nipple globally denoted by the reference (1) and comprising a riser tube (2) which merges into a neck (4) surrounding the dispensing orifice (3). A shoulder (5) is formed circularly around the neck (4) and merges into a container wall (6). For example, the container wall (6) is the wall of a laminate tube. FIG. 1 shows the upper part of a tube of the type known from conventional toothpaste tubes for dispensing striped toothpaste. Now, in contrast to these conventional tubes, the cross-section of the nipple (1) widens and changes at the transition of the riser tube (2) to the neck (4) where the shoulder (5) also surrounds the neck (4). Whereas the riser tube (2) has a cylindrical cross-section, so that a round strand of a product B is transported through the riser tube (2), the cross-section of the outlet opening (3) widens to a square cross-section in the region of the neck (4). Four perforations (7) distributed around the inner periphery are formed in the transition zone from the riser tube (2)—arranged concentrically to the outlet opening (3)—to the neck (4). These perforations (7) are situated exactly at the four corners of the square outlet opening (3) surrounded by the neck (4). Leading past the longitudinal edges of the perforations (7), narrow bars (8) are formed over the length of the rise tube (2) to just below the upper edge of the neck (4), projecting slightly from the inner surface of the riser tube (2) and neck (4) and forming narrow passages (9). A stripe paste A is conveyed in these passages (9) above the perforations (7).

Figure 1:
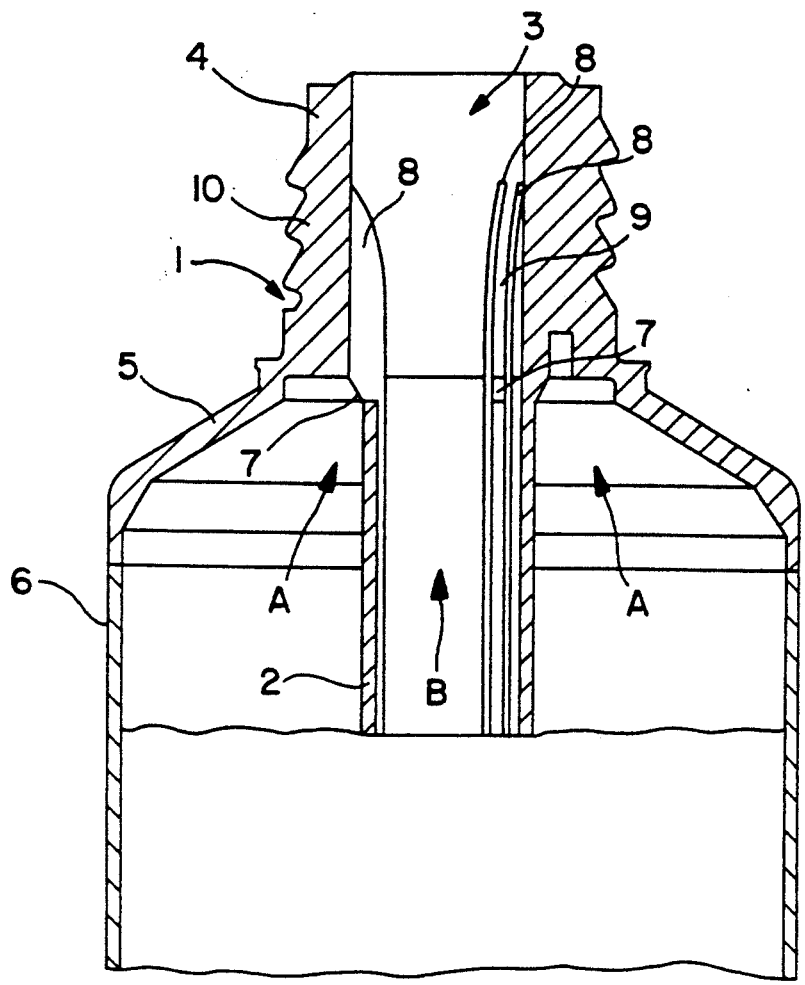
FIG. 1 is a longitudinal section through the device.
Figure 2:
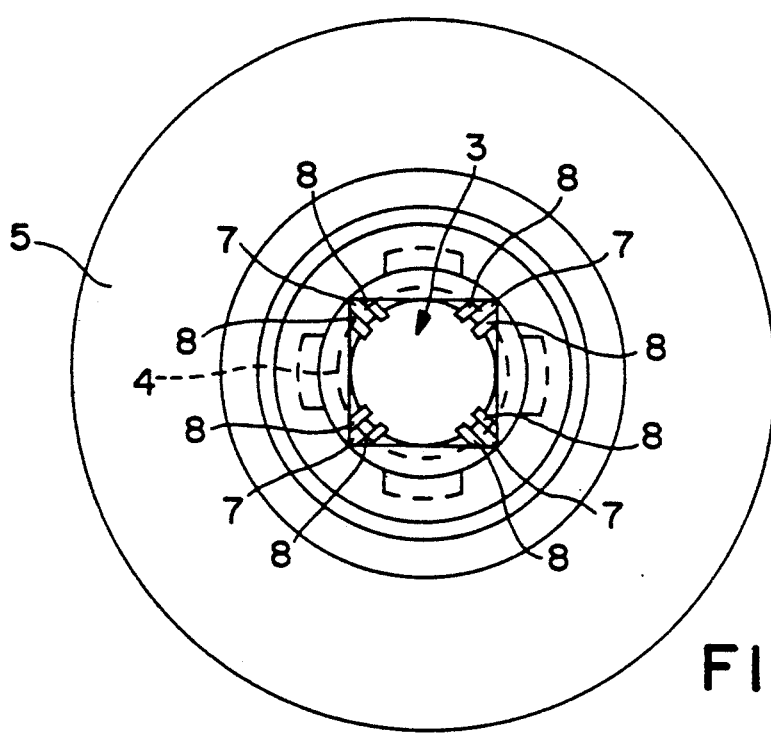
FIG. 2 is a plan view.

Accommodated in the container surrounded by the container walls (6), normally as far as the lower edge of the riser tube (2), is a carrier strand paste B, the stripe paste A normally being situated in the remaining annular space between the outer surface of the riser tube (2) and the container wall (6) and also below the shoulder (5). Overall, 95% of such a container is normally filled with the carrier strand paste B and 5% with the stripe paste A.

If, now, pressure is applied to the carrier strand paste B (where the container wall (6) is flexible, normally by finger pressure from outside), the carrier paste B transmits this pressure to the stripe paste A, the carrier strand paste B and the stripe paste A entering the container opening (3) respectively through the riser tube (2) and through the perforations (7). By virtue of the configuration of the neck (4), a square strand of toothpaste is formed therein, its corner edges being formed by the stripe paste A. If the carrier strand paste and the stripe paste are given different colors, a toothpaste strand with color-contrasted stripes at the corner edges is obtained.

The neck (4) is formed on its outer surface with a screw thread (10) onto which a typical closure may be screwed to close the outlet opening (3).

EXAMPLES

The following formulation examples are intended to illustrate the invention without limiting it in any way.

BASIC TOOTHPASTE MIXTURE

For formulating a toothpaste according to the invention, the following transparent basic mixture is initially prepared:

| Component | Parts by weight |
| --- | --- |
| Precipitated silica SIDENT 12 DS[1] | 19.00 |
| Aerogel silica FK 300 DS[2] | 2.00 |
| Sorbitol (70% solution in water) | 45.00 |
| Glycerol (86% solution in water) | 18.00 |
| Water | 7.77 |
| Polyethylene glycol 300[3] | 2.00 |
| Blanose TM refined CMC 7M2[4] | 0.40 |
| Sodium lauryl sulfate | 1.50 |
| Sodium fluoride | 0.23 |
| Hydroxybenzoic acid methylester | 0.10 |
| Saccharin | 0.30 |
| Flavorings | 0.90 |

[1](DEGUSSA)
[2](DEGUSSA)
[3](HÜLS)
[4]Carboxymethyl cellulose sodium salt (AQUALON)

Tis basic mixture was used to formulate the following toothpastes (quantities in parts by weight):

| 1. Toothpaste with a translucent carrier strand paste and an opaque stripe paste | | |
| --- | --- | --- |
|  | Carrier strand paste | Stripe paste |
| Basic mixture | 97.2 | 97.2 |
| Sorbitol (70% in water) or glycerol (86% in water) | — | 2.0 |
| Water (fully deionized) | 2.1 | — |
| Titanium dioxide | — | 0.8 |
| Aerogel silica FK 300 DS | 0.7 | — |
| Dyes | <0.05 | <0.05 |
| Yield point (Pa) at 20° C. | 257 | 222 |
| Viscosity (Pa.s) at 20° C. | 0.02 | 0.02 |

| 2. Toothpaste with transparent carrier strand and stripe pastes | | |
| --- | --- | --- |
|  | Carrier strand paste | Stripe paste |
| Basic mixture | 98.0 | 98.0 |
| Sorbitol (70% in water) or glycerol (86% in water) | — | 2.0 |
| Water (fully deionized) | 1.3 | — |
| Aerogel silica FK 300 DS | 0.7 | — |
| Dyes | <0.05 | <0.05 |
| Yield point (Pa) at 20° C. | 227 | 200 |
| Viscosity (Pa.s) at 20° C. | 0.02 | 0.03 |

The viscosity measurements were carried out with the Haake Rotovisco RV 12 system using an SV II St measuring instrument and a 150 measuring head. A Haake Rheocontroller was used to control the drive of the measuring head.

The measurement was carried out at a temperature of 20° C. To this end, the shear rate was first continuously increased from $D=0$ to 128 min$^{-1}$ over a period of 180 seconds (upward shear cycle). After a holding time of 6 seconds at $D=128$ min$^{-1}$, the shear rate was continuously reduced from 128 to 0 min$^{-1}$, over a period of 180 seconds.

If the correlation observed between shear rate and shear stress is recorded in the form of a graph, a hysteresis curve was generally obtained.

The output signals of the Rotovisco RV 12 were fed via an interface into a computer in which they were evaluated. To this end, the yield point at $D=0$ was calculated from the measured values for the shear stress at $D=32$ min$^{-1}$ and $D=128$ min$^{-1}$ by a regression calculation based on the Casson equation.

The figures for the yield points and viscosities in the above Tables are based on the upward shear cycle. These figures represent values which the toothpastes achieve after storage for about 1 week and which do not change within the limits of measurement accuracy during further storage. Normally, distinctly lower yield point values and distinctly higher viscosity values are measured immediately after production of the toothpastes. These values initially change considerably within the first few hours and days, reaching the final levels shown asymptotically after about one week.

What is claimed is:

1. A toothpaste contained within capable of being dispensed from an outlet opening having a rectangular or square cross sectional area in a container in the form of a multicolored, striped strand, said multicolored, striped strand consisting of a carrier strand paste and at least one rectangular or square stripe paste differing in color from the carrier strand paste, wherein (a) the ratio between the yield points of the carrier strand paste and the stripe paste is approximately 1.10:1 to 1.20:1, (b) the toothpaste is in the shape of a strand with a cross-section in the form of a 4-sided polygon, (c) the toothpaste is free from a diffuse transition zone between the carrier strand paste and the stripe paste, and (d) the rectangular or square strand cross-section is stable said toothpaste strand and said carrier strand having different and contrasting colors, and each, by virtue of the configuration of the outlet, is formed rectangular or square, and thereby has an improved hold on the toothbrush.

2. A toothpaste as claimed in claim 1, wherein the ratio between the yield points of the carrier strand paste and the stripe paste is from 1.12:1 to 1.18:1.

3. A toothpaste as claimed in claim 1, wherein the carrier strand paste and the stripe paste differ solely in their contents of materials selected from the group consisting of water, polyalcohols, silica, dyes, and pigments.

4. A toothpaste as claimed in claim 3, wherein the carrier strand paste and the stripe paste differ solely in their contents of materials selected from the group consisting of water, sorbitol, glycerol, and silica.

5. A toothpaste as claimed in claim 1, which contains the carrier strand paste and the stripe paste in a ratio by volume of from 92:8 to 97:3.

6. A toothpaste as claimed in claim 1 in the shape of a strand with a cross-section in the form of a rectangle.

7. A toothpaste as claimed in claim 2, wherein the carrier strand paste and the stripe paste differ solely in their contents of materials selected from the group consisting of water, polyalcohols, silica, dyes, and pigments.

8. A toothpaste as claimed in claim 7, wherein the carrier strand paste and the stripe paste differ solely in their contents of materials selected from the group consisting of water, sorbitol, glycerol, and silica.

9. A toothpaste as claimed in claim 2, which contains the carrier strand paste and the stripe paste in a ratio by volume of from 92:8 to 97:3.

10. A toothpaste as claimed in claim 2 in the shape of a strand with a cross-section in the form of a rectangle.

11. A toothpaste as claimed in claim 3, which contains the carrier strand paste and the stripe paste in a ratio by volume of from 92:8 to 97:3.

12. A toothpaste as claimed in claim 8, which contains the carrier strand paste and the stripe paste in a ratio by volume of from 92:8 to 97:3.

13. A toothpaste as claimed in claim 7, which contains the carrier strand paste and the stripe paste in a ratio by volume of from 92:8 to 97:3.

14. A toothpaste as claimed in claim 4, which contains the carrier strand paste and the stripe paste in a ratio by volume of from 92:8 to 97:3.

* * * * *